US005611814A

United States Patent [19]
Lorenc

[11] Patent Number: 5,611,814
[45] Date of Patent: Mar. 18, 1997

[54] RESORBABLE SURGICAL APPLIANCES AND ENDOSCOPIC SOFT TISSUE SUSPENSION PROCEDURE

[76] Inventor: Z. Paul Lorenc, 52 East End Ave., Apt. 35A, New York, N.Y. 10028

[21] Appl. No.: 340,710

[22] Filed: Nov. 16, 1994

[51] Int. Cl.$^6$ ................................................ A61B 17/08
[52] U.S. Cl. ................... 606/213; 606/151; 606/204.35; 128/898
[58] Field of Search .................................. 606/1, 61, 72, 606/73, 77, 151, 191, 204.35, 212, 215, 216, 218, 219, 230, 232, 139; 411/388, 398, 400, 401, 907, 908; 128/898

[56] References Cited

U.S. PATENT DOCUMENTS

| | | | |
|---|---|---|---|
| 5,067,955 | 11/1991 | Cotrel | 606/61 |
| 5,261,914 | 11/1993 | Warren | 606/73 |
| 5,275,601 | 1/1994 | Gogolewski | 606/72 |
| 5,417,533 | 5/1995 | Lasner | 411/426 |
| 5,443,482 | 8/1995 | Stone et al. | 606/232 |

FOREIGN PATENT DOCUMENTS 0502698  3/1992  European Pat. Off. .

*Primary Examiner*—Michael Powell Buiz
*Assistant Examiner*—Patrick W. Rasche
*Attorney, Agent, or Firm*—Aufrichtig Stein & Aufrichtig, P.C.

[57] ABSTRACT

A resorbable surgical appliance for use in supporting soft tissue in a superior position in the body. The surgical appliance includes a coupling member that connects the surgical appliance to a bone or hard tissue and a gripping member or members secured to the coupling member selectively gripping soft tissue and retaining the soft tissue in a superior position. The connected coupling member and gripping member are formed from a resorbable mixture which maintains a specified percentage of the connection strength with the bone or hard tissue for a period of time at least equal to a healing period. Thereafter, the surgical appliance is substantially resorbed by the body over a period of time created for healing. The surgical appliance is particularly adapted for use in endoscopic brow lift surgery and other endoscopic cosmetic, plastic and reconstructive surgical procedures.

9 Claims, 3 Drawing Sheets

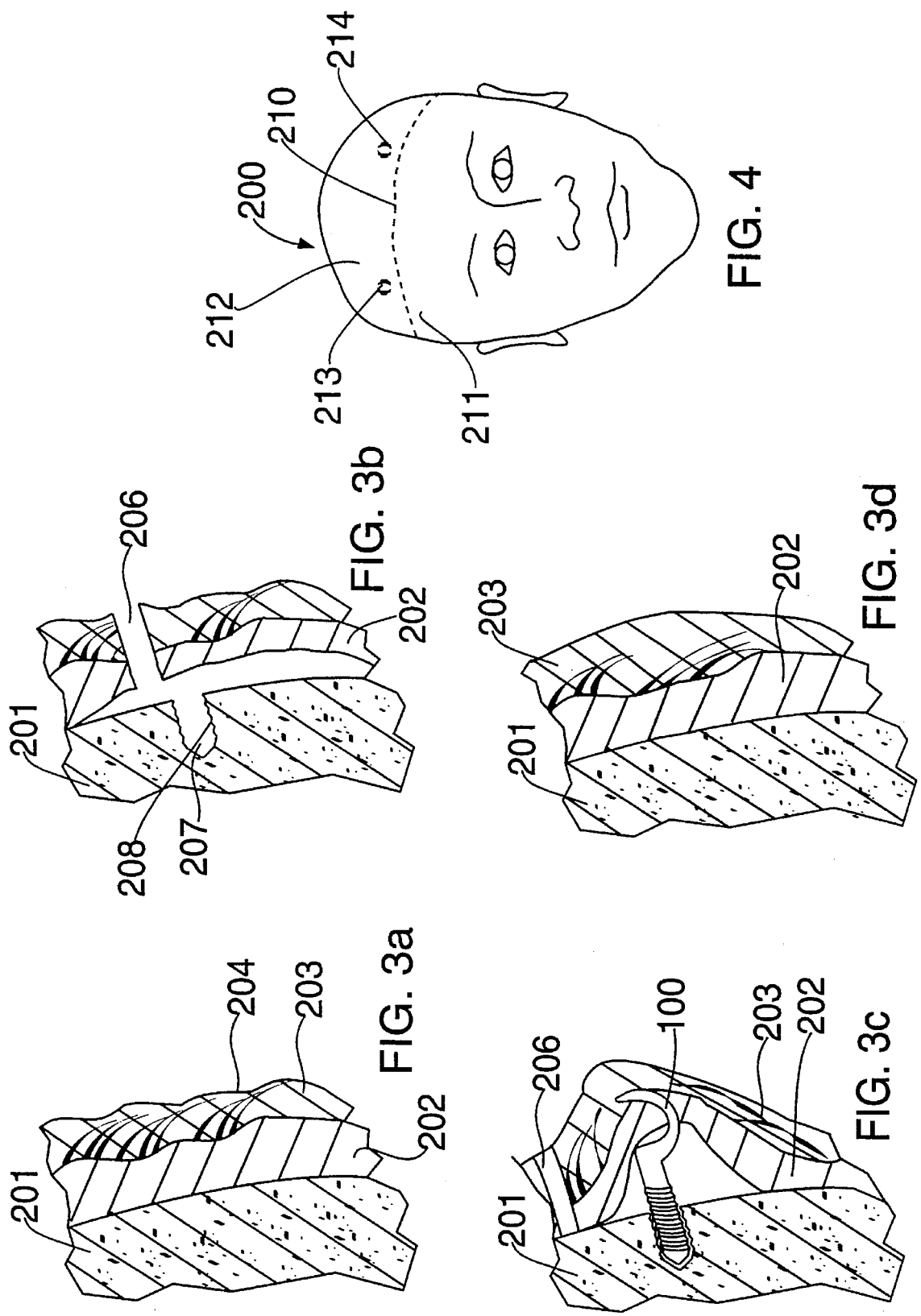

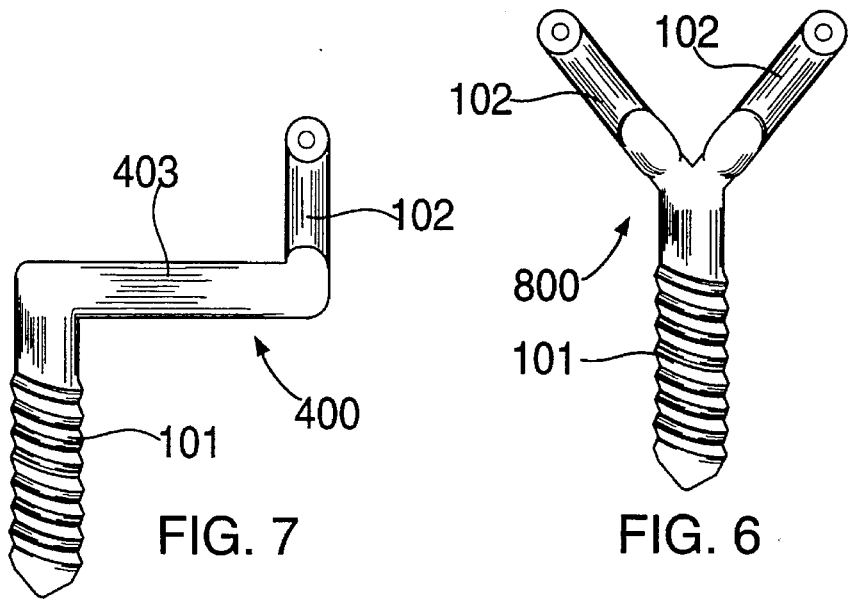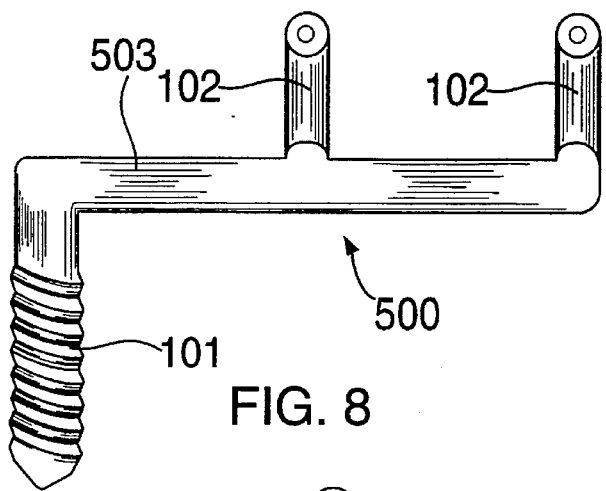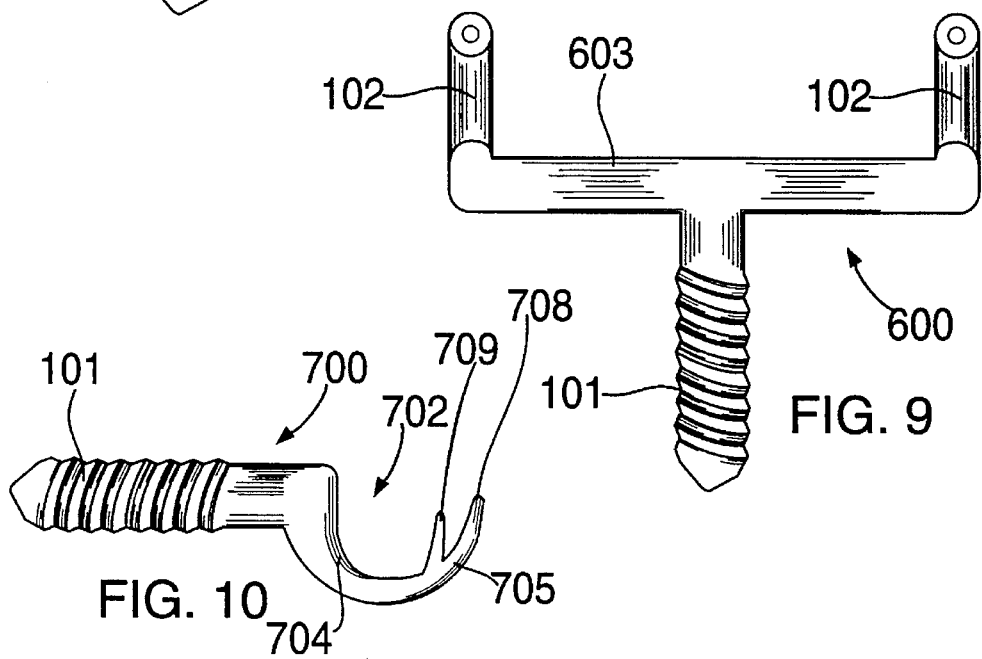

RESORBABLE SURGICAL APPLIANCES AND ENDOSCOPIC SOFT TISSUE SUSPENSION PROCEDURE

BACKGROUND OF THE INVENTION

The invention is generally directed to the use of resorbable suspension devices in connection with plastic surgery and related surgical procedures and in particular to a new resorbable appliance and the use of a resorbable appliance for use in connection with endoscopic brow lift surgery and similar procedures.

In the past, various approaches have been used to shift and hold soft tissue in place during the course of plastic surgery modification of a patient's anatomy. A brow lift procedure is used to eliminate the generally horizontal lines on a patient's forehead at rest by elevating the top of the patient's brow from the skull and suspending the brow in a superior position for a sufficient period of time so that the soft tissue of the scalp and connective tissue knits in place, leaving the patient with an unlined brow. In the past, invasive surgery using standard surgical cutting tools and open surgical sites using a scalpel have resulted in large entry wounds which tend to create large scars which must be hidden, where possible, under the patient's hairline. However, in many cases, the patient's hairline is inadequate as a means for camouflaging the surgical incision and as a result, these operations were generally not favored due to the complications as well as the large scars which would result.

As the state of the art of surgery improved, it became possible to conduct the brow lift surgery with the use of an endoscope which allows the physician to make a small incision and then extend the tools to be utilized through the small slit and view the work area with the endoscope and complete the surgery without the need for a large surgical incision. The endoscope is similar to the arthroscope utilized in connection with surgery conducted on the knees, shoulders and elbows. In the traditional surgery the soft tissue of the scalp above the brow is held in place by an outside support. Recently, surgical pins or posts have been put in place in the skull to anchor the soft tissue in place. After a period of time following the completion of the healing process, during which the soft tissue is firmly bonded into its new location, the surgeon must reenter the site, remove the pin or post and then reclose the incision. This procedure increases the risk of infection as a substantial risk of infection exists each time an incision is made. In addition, the volume occupied by the removed pin creates an internal space susceptible to collection of fluids and other undesired results. Furthermore, the patient must return and must again suffer the pain or at least discomfort of further incision including the risk of anesthesia whether local or general as well as the need to have further bandages. In some cases it is possible to permanently leave the metal posts or pins in the wearer's skull. However, for purely cosmetic procedures such as the brow lift, most patients are reluctant to have metal pins or posts inserted into their skull, either to remain forever or to be removed at some later date.

As an improvement to the basic brow lift surgery conducted with traditional surgical techniques, the applicant herein has developed a system for endoscopic brow lifts incorporating a portion of a surgical pin cut to the appropriate lengths. Each of these pins is inserted through incisions made through the scalp in connection with the endoscopic procedure to suspend parts of the patient's scalp. Finally, after the tissue has healed in place and the edema has gone down, another endoscopic procedure is required to remove the pins. Again, the risks inherent in reentry are present as well as the discomfort, inconvenience and additional cost to the patient for a second, albeit smaller, surgical procedure.

Accordingly, there is the need for an improved surgical appliance for supporting soft tissue in a specified fixed location in which the surgeon would only need to once invasively enter the patient's body. It is desired to have the material utilized to suspend the soft tissue or scalp be formed of a material which has the appropriate structural requirements necessary to retain the soft tissue under tension in place and that those characteristics be maintained for a sufficient time to allow complete healing. Thereafter the appliance should be absorbed by the body naturally over a period of time so that no further surgical procedure is necessary.

SUMMARY OF THE INVENTION

The invention is generally directed to a surgical appliance for use in supporting soft tissue in a superior position in the body. The surgical appliance includes a coupling member adapted to connect the surgical appliance to a bone or hard tissue. A gripping member or members secured to the coupling member selectively grips soft tissue and retains the soft tissue in a superior position. A resorbable mixture is used to form the coupling and gripping members so that the coupling member maintains a specified percentage of a connection strength with the bone or hard tissue for a period of time at least equal to a healing period. The gripping member grips the soft tissue so as to retain the soft tissue in a superior position for a period of time at least equal to the healing period. Thereafter, the surgical appliance is substantially resorbed by the body over a period of time greater than the healing period. As a result, in a single procedure the surgical appliance may be inserted, enable movement of the soft tissue to a superior position and retain the soft tissue's superior position for a healing period without the need for a second procedure to remove the surgical appliance or the permanent presence of the surgical appliance in the body.

Another object of the invention is a surgical procedure for supporting soft tissue in a superior position in the body without the need for a second procedure to remove a surgical appliance or the permanent presence of the surgical appliance in the body. An incision is made through the skin and soft tissue to a supporting structure, a hole is drilled and tapped in the supporting structure, a resorbable surgical appliance having a threaded end and a gripping end is screwed into the tapped hole in the support structure. Next, the soft tissue is biased toward the superior position and the soft tissue is draped in place by the gripping member. The incision is closed and the surgical appliance holds the soft tissue in the superior position for at least a period of time equal to a healing period. Thereafter, over a period of time the surgical appliance is absorbed by the body so that the superior position of the soft tissue is permanently retained without the need for further procedures or the continuing presence of a surgical appliance.

Another object of the invention is to provide an improved resorbable surgical appliance for endoscopic brow lift surgeries.

Yet a further object of the invention is to provide improved resorbable surgical appliances for use, in pairs in connection with endoscopic brow lift surgery whereby minute incisions in a single procedure can cure brow furrows without the need for further procedures to remove surgical appliances, external support or the permanent presence of surgical appliances in the body.

Still another object of the invention is to provide an improved resorbable surgical appliance for use in plastic surgery for anchoring the brow in a new, more superior position as in an endoscopic brow lift.

Yet a further object of the invention is to provide improved resorbable surgical appliance for use in anchoring the face (as in a face lift) in a more youthful position.

Still another object of the invention is to provide an improved surgical appliance for suspending any soft tissue such as skin, muscle and/or fascia, from a bony prominence as in reconstructive surgery.

Still yet another object of the invention is to provide an improved resorbable surgical appliance for use in scalp surgery (as in scalp reduction for hair loss) to anchor the scalp and minimize scars by diverting tension from wound edges and giving a better scar.

Yet a further object of the invention is to provide an improved surgical appliance for supporting soft tissue so as to minimize scar formation by diverting tension from wound edges and giving a less substantial scar formation and a cleaner healing of the skin tissue.

Yet still a further object of the invention is to provide an improved absorbable surgical appliance for use in a body form maintaining soft tissue in a superior position under tension for a sufficient period time for the soft tissue to retain its superior position without support and thereafter for the surgical appliance to be absorbed by the body.

Still yet another object of the invention is to provide an improved operating procedure for endoscopically lifting a patient's brow utilizing an absorbable surgical appliance which screws into adjacent portions of the skull and, after the brow has rehealed in a superior position is absorbed completely by the body.

Still other objects and advantages of the invention will in part be obvious and will in part be apparent from the specification.

The invention accordingly comprises the features of construction, combinations of elements, arrangements of parts, series of steps and identification of procedures which will be exemplified in the constructions and procedures hereinafter set forth and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3A is an enlarged partial cross-sectional view taken along a vertical line showing the brow and skull region to receive the surgical appliance prior to the procedure;

FIG. 3B is a cross-section similar to the cross-section of FIG. 3A following creation of an endoscoping work incision, the drilling of a small hole in the skull and the tapping of the drilled hole;

FIG. 3C is a cross-sectional view similar to the cross-sectional view of FIG. 3A showing the soft tissue of the scalp and brow separated from the skull and the soft tissue of the brow and scalp is pulled up and secured on the hook end of the surgical appliance;

FIG. 3D is a cross-sectional view similar to FIG. 3A after the surgical appliance has been absorbed by the body;

FIG. 4 is a front elevational view of a patient's head showing the outward manifestation of the surgical procedure following its completion;

FIG. 6 is a front elevational view of a surgical appliance constructed in accordance with another preferred embodiment of the invention;

FIG. 7 is a front elevational view of a surgical appliance constructed in accordance with another preferred embodiment of the invention;

FIG. 8 is a front elevational view of a surgical appliance constructed in accordance with a further preferred embodiment of the invention;

FIG. 9 is a front elevational view of a surgical appliance constructed in accordance with another preferred embodiment of the invention; and FIG. 10 is a perspective view of an alternate embodiment of the surgical appliance constructed in accordance with another preferred embodiment of the invention.

DETAILED DESCRIPTION OF THE PREFERRED EMBODIMENTS

Figure 1:
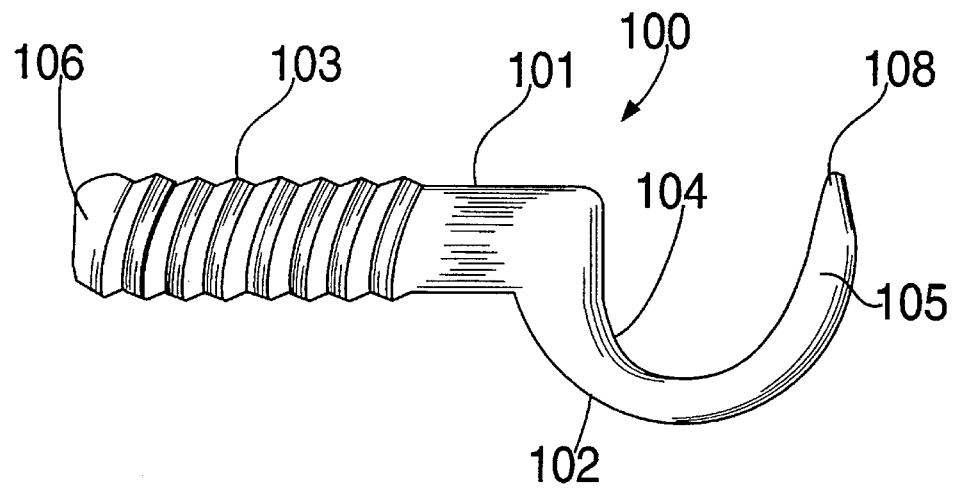
FIG. 1 is an enlarged perspective view of a resorbable surgical appliance constructed and arranged in accordance with a preferred embodiment of the dimension.
Figure 2:
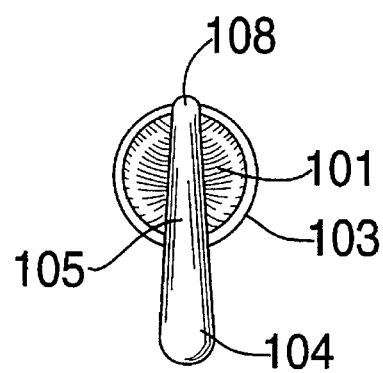
FIG. 2 is a right side view of the surgical appliance of FIG. 1.

Reference is made to FIGS. 1 and 2 wherein a resorbable surgical appliance, generally indicated as 100 constructed in accordance with preferred embodiment of the invention is depicted. Surgical appliance 100 includes a connective portion 101 and a gripping portion 102. Connective portion 101 has a threading 103 about its circumference. Connective section 101 has a generally round cross-section from end 106 to rounded hook portion 107. End 106 is shown as terminating in a frustumated cone and not a sharp point. However, as shown in other embodiments below, end 106 can also be formed with a tapered end coming to a point. Gripping end 102 has curved portion 107 which is directly adjacent connected portion 101 and terminates in hook point portion 105. Hook point portion 105 is shown as terminating in a generally pointed end, generally aligned with the base of connected portion 101 at the point at which it joins rounded portion 107. In other preferred embodiments, as shown below, hook portion 105 may either extend further so that it extends beyond the imaginary continuation of connective portion 101 or may be smaller and terminate within the imaginary extension of cylindrical portion 101. As best seen in FIG. 2, the tip 108 of hook portion 105 is in line with a cylindrical connected portion 101. Likewise, the curved section 107 extends above the top of cylindrical connective portion 101. These connections can be modified based upon the specific needs of the surgical procedure involved.

Surgical appliance 100 is formed of a resorbable mixture which is absorbed by the body over a period of time. Generally, the length of time over which the resorbable material deteriorates within the body is controlled so that the surgical appliance retains a required percentage of its holding strength for holding soft tissue for skull tissue in the desired superior position for a sufficient time for the soft tissue or scalp tissue to reestablish contact with the surrounding harder tissues or bones and knit naturally so that upon degradation and absorption of the surgical appliance the soft tissue or scalp tissue will not move from the superior position it has been placed at during the surgical procedure.

In a preferred embodiment, surgical appliance 100 is formed of a blend of polylactic acid and polyglycolic acid in combination adjusted so as to assure that at least 70% of the initial holding power of the surgical appliance is maintained for a healing period and thereafter after an absorption period, the complete surgical appliance has been absorbed.

In a preferred embodiment surgical appliance 100 should maintain at least 50% of its holding power for the healing period, in a more preferred embodiment the initial holding power should be maintained within a range of at least 60%–80% of the holding power and an even more preferred embodiment at least 70% of the initial holding power is maintained for the holding period.

In a preferred embodiment the holding period is at least three weeks, preferably four to eight weeks and even more preferably at least six weeks. Finally, the material should fully absorb preferably within one year, more preferably within six to ten months and even more preferably within about nine months. These optimum levels are based upon use of the surgical appliance in connection with endoscopic brow lift surgery. Different optimum periods and percentages of holding power will be necessary depending upon the nature of the surgery contemplated.

By varying the composition of the materials the absorption of the material utilized can be affected so as to either enhance or delay absorption.

Reference is next made to FIGS. 3A–3D and 4 in which a procedure for endoscoping brow lift surgery is generally depicted. The drawings are of a basic, sketch-like variety and are not intended to accurately reproduce the underlying structures, blood vessels, nerve fibers and tissue structure found at or about the brow and skull of an actual patient.

FIG. 3A shows the brow region of the patient in side cross-section, generally showing a furrowed brow prior to an endoscopic brow lift surgical procedure. Generally, the figure shows a human head generally indicated as 200 including skull 201, soft tissue 202, scalp 203 and furrows 204.

In FIG. 3B, a small incision 206 is made above the hairline 210 (FIG. 4) and the endoscope (not shown) is inserted. The endoscope is a well known tool for viewing and controlling delicate surgery performed through a small slit, rather than a large incision in which the field of activities is exposed. The soft tissue 202 and scalp 203 are elevated through the visual control available as a result of the endoscope's use. This elevation is also conventionally performed. In the embodiment of FIG. 3B a small hole 207 has been drilled into skull 206 and hole 207 has had threading 208 added to it by a tapping device which is conventionally available.

Reference is next made to FIG. 3C wherein surgical appliance 100 is introduced into tapped hole 207. Leading end 106 is placed in the opening of the hole and appliance 100 is screwed in until the appropriate depth of connection and appropriate extension of gripping end 102 is achieved.

Also in FIG. 3C the scalp 203 and soft tissue, 202 are stretched upward so as to remove the furrows 204 in scalp 202. The inside of soft tissue 202 and scalp 203 are grabbed and pierced by the hook 105 and hook end 108 so that there is a snug and secure connection and tensile pressure holding the soft tissue 202 and scalp 203 taut and smooth over the visible portion of the patient's brow. The tip 108 does not protrude from the outside of scalp layer 203.

Finally, FIG. 3D shows the final stage of the procedure following the period during which the scalp and other soft tissue has been held in the new, superior position up against scalp 201 for a sufficient healing period, generally for at least three weeks preferably four to six weeks and even more preferably for at least six weeks. Thereafter, as the resorbative material of surgical appliance 100 is absorbed after an absorption period which is preferably under a year, even more preferable, six to twelve months and even more preferably by about nine months, surgical appliance 100 has been completely absorbed by the patient's body, the bone mass drilled out in hole 207 has grown back and no evidence of the procedure remains other than the smooth outer brow surface desired. Scalp 203 and soft tissue 202 heals and knits firmly with the bony surface of skull 201 along the brow in the new, superior position enabled and maintained by surgical appliance 100 during its period of residence within the brow region.

In a preferred embodiment the entire length of surgical appliance 100 is 6 millimeters, the length of the connective or threaded portion is 2 millimeters and the length of the supporting portion is 4 millimeters. Gripping portion 102 has a height, perpendicular to the horizontal extent of threaded portion 101 of 4 millimeters. The diameter of threaded portion 101 is 2 millimeters. As noted above, these dimensions may vary depending upon the nature and extent of the surgery involved.

Reference is next made to FIG. 4 wherein a frontal view of a patient after undergoing the endoscopic brow lift surgery in accordance with the preferred embodiment described above including use of resorbtive surgical appliance 100 is depicted. As seen in FIG. 4 the head 200 includes the hairline 210 separating the exposed brow portion 211 from hair covered portion 212. In hair covered portion 212, two small protrusions 213, 214 are present which signify the locations at which two surgical appliances 100 are seated above the hairline 210 providing a smooth brow surface 211.

Over time the bumps or protrusions 213 and 214, which are caused by the outward extension of surgical appliances 100, recede as surgical appliance 100 is absorbed by the body. After the surgical appliances 100 are fully absorbed, the bumps will completely disappear and leave no further evidence of their existence. The operation can even be performed on individuals with limited or no hair in view of the tiny incision initially made and the only minor visibility of the bumps 213, 214.

Figure 5:
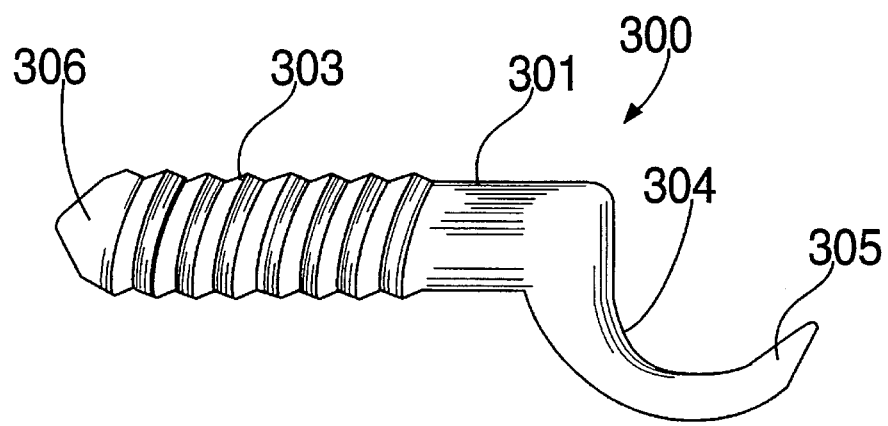
FIG. 5 is a perspective view of a surgical appliance constructed in accordance with another embodiment of the invention.

Reference is next made to FIG. 5 wherein a surgical appliance generally indicated as 300 constructed in accordance with another preferred embodiment of the invention is depicted, like reference numerals depicting like elements. Surgical appliance 300 includes a connective region 101 by having screw portion 103 and end portion 306 coming to a tapered point. This is contrasted with surgical appliance 100 in which tip 106 ends in a flattened surface. Also, rounded portion 302 includes a shortened rounded section 304 and hook portion 305. Rather than extending with a full hook back up to the top surface of surgical appliance 300 as is done with hook point 108 of hook 105 in surgical appliance 100 of FIG. 1, less curvature is present. This hook structure may be similarly utilized with other appliance forms as shown in FIGS. 6–10.

Reference is next made to FIG. 6 wherein a surgical appliance, generally indicated as 800, constructed in accordance with another preferred embodiment of the invention is depicted. Surgical appliance 800 includes a screw portion 101 and two hook portions 102 at right angles to each other. Depending upon the needs of the surgical procedure greater or lesser interior angles can be established. Also, the hook portions 102 can be placed on a single screw portion 101 for even greater stability and strength.

Reference is next made to FIG. 7 wherein a surgical appliance generally indicated as 400 constructed in accordance with another preferred embodiment of the invention is depicted. Surgical appliance 400 includes a screw portion 101 and a hook portion 102 connected by a lateral displacement bar section 403 which allows the hook 102 to be displaced from the position at which the screw hole is placed. Bar 403 may be made of varying lengths depending upon the displacement intended or required under the circumstances of the procedure. Often, no suitable bone or hard tissue is present at the point that the soft tissue must be moved to a superior position and the surgical appliance 400 provides the flexibility to adapt the use of a resorbable surgical appliance to such procedure.

Reference is next made to FIG. 8 wherein a resorbable surgical appliance generally indicated as 500 constructed in accordance with another preferred embodiment of the invention is depicted, like reference numerals representing like elements. Surgical appliance 500 includes a screw or connector end 101 and two hook gripping portions 102 spaced along a connective bar 503 on one side of screw portion 101. Again, depending upon the circumstances and nature of the procedure and the availability of appropriate bone structures to support the surgical appliance, two or more hook portions 102 may be spaced along the length of bar 503.

Reference is next made to FIG. 9 wherein a surgical appliance generally indicated as 600 constructed in accordance with another preferred embodiment of the invention is depicted, like reference numerals representing like elements. Surgical appliance 600 includes a screw portion 101 and two hook portions 102 spaced apart along horizontal support bar 603. Surgical appliance 600 allows for two portions of soft tissue to be suspended from a single surgical appliance. The hook portions 102 may also be made smaller so that less displacement away from the bone surface is provided. In addition to the structure shown, two or more hook portions 102 may be added on each side of screw portion 101 as required in connection with each procedure. It is not necessary that the hooks be either symmetrically or regularly placed. Rather, the hooks can be placed where required for each specified surgical procedure.

Reference is next made to FIG. 10 wherein a surgical appliance generally indicated as 700 constructed in accordance with another embodiment of the invention is depicted, like reference numerals representing like elements. Surgical appliance 700 includes a screw portion 101 and a hook portion 702 having a rounded portion 704 and a hook portion 705. Hook portion 705 includes a primary point 708 and an additional barb 709 to provide additional gripping power. Various fish hook or other types of barbs may be utilized to increase the holding power of the surgical appliance as necessary.

The surgical appliance 100 and the variations thereof identified as surgical appliances 300, 400, 500, 600 and 700 may be modified and constructed of various sizes and shapes as required by the parameters and needs of varying types of surgical, procedures. In connection with the endoscopic brow lift surgery, in a preferred embodiment the entire surgical appliance 100 has a length of about 10 millimeters of which 6 millimeters represents the screw portion 101 and 4 millimeters represents the length of the hook portion 102. Hook portion 102 also has a height from the tip 108 of the hook point 105 to the base of rounded portion 104 of about 4 millimeters. Screw portion 101 also has a diameter of about 2 millimeters. Smaller or larger dimensions may be made depending upon the varying needs, strengths and positions in which surgical appliances 100 and related variations thereof 300, 400, 500, 600 and 700 are utilized. Each of the surgical appliances disclosed and described may also be utilized in varying ways in varying procedures to provide an improved method for retaining soft tissue, skin and scalp at superior positions in connection with cosmetic, plastic and reconstructive surgery. In addition, particularly in connection with operations which traditionally leave substantial and large scars, the surgical appliances disclosed herein may be used to relieve and reduce tension at the major incision areas so as to aid in more effective healing of the incision with reduced scar tissue formation.

Currently, the endoscopic brow lift surgery is disfavored as a cosmetic surgery in view of the current procedure's failure to provide required cosmetic reparation without either substantial risk of collateral injury related to infection or the need for further surgical procedures to remove surgical appliances after the healing period has been completed. This of course makes a patient susceptible to further risk of infection or anesthetic related problems. Accordingly, an improved surgical appliance which is resorbable and provides improved results in connection with endoscopic brow lift surgery and other surgical procedures is provided.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It will also be understood that the following claims are intended to cover all of the generic and specific features of the invention herein described and all statements of the scope of the invention which, as a matter of language, might be said to fall therebetween.

What is claimed is:

1. A surgical appliance for use in supporting soft tissue in a position superior to its natural state in a body, the surgical compliance comprising:

coupling means adapted to connect the surgical appliance to a bone or hard tissue;

gripping means secured to the coupling means for selectively gripping soft tissue and retaining the soft tissue in the superior position, wherein the gripping means includes two hooking members;

resorbable means for forming the coupling and gripping means so that the coupling means maintains a required connection strength with the bone or hard tissue for a period of time at least equal to a healing period, the resorbable means including a resorbable material, the gripping means grips the soft tissue so as to retain the soft tissue in the superior position for a period of time at least equal to the healing period, and for causing the surgical appliance to be substantially resorbed by the body after the healing period;

whereby in a single procedure the surgical appliance may be inserted and enable movement of the soft tissue to a superior position and retention of the soft tissue in said superior position for a healing period, without the need for a second procedure to remove the surgical appliance or the permanent presence of the surgical appliance in the body.

2. The surgical appliance of claim 1 wherein the two hooking members are angled apart by 90°.

3. The surgical appliance of claim 1 further comprising extender means for connecting and displacing the coupling means and the gripping means, the extender means being formed from the resorbable means.

4. A surgical appliance for use in supporting soft tissue in a position superior to its natural state in a body, the surgical appliance comprising:

coupling means adapted to connect the surgical appliance to a bone or hard tissue;

gripping means secured to the coupling means for selectively gripping soft tissue and retaining the soft tissue in the superior position, wherein the gripping means includes at least two separate hook members secured to the extender means;

resorbable means for forming the coupling and gripping means so that the coupling means maintains a required connection strength with the bone or hard tissue for a period of time at least equal to a healing period, the resorbable means including a resorbable material, the gripping means grips the soft tissue so as to retain the soft tissue in the superior position for a period of time at least equal to the healing period, and for causing the surgical appliance to be substantially resorbed by the body after the healing period;

extender means for connecting and displacing the coupling means and gripping means, the extender means being formed from the resorbable means;

whereby in a single procedure the surgical appliance may be inserted and enable movement of the soft tissue to a superior position and retention of the soft tissue in said superior position for a healing period, without the need for a second procedure to remove the surgical appliance or the permanent presence of the surgical appliance in the body.

5. The surgical appliance of claim 4 wherein the extendor means extends perpendicular to the coupling means and hook members are found on both sides of the coupling means.

6. The surgical appliance of claim 4 wherein the gripping means includes a hook having a primary point and an additional barb.

7. A surgical procedure for supporting soft tissue in an improved position in a body incorporating a resorbable surgical appliance, the procedure comprising:

making a small entry slit proximate to soft tissue to be moved;

inserting an endoscope into the small opening for viewing surgical activity under skin;

separating the soft tissue and skin from a bone;

drilling a hole in a bone tissue proximate the soft tissue to be moved;

tapping threads into the hole;

screwing a resorbable surgical appliance, having a threaded end and a hook end, into the threaded hole;

moving the soft tissue to a desired superior position and draping the soft tissue over the hook portion of the surgical appliance so that the hook end pierces the soft tissue and retains it under tension in the desired improved position;

closing the entry slit;

whereby the soft tissue is maintained in the improved position for at least a healing period by the resorbable surgical appliance which thereafter is resorbed by the patient's body with the bone regrowing to fill the tapped hole following the resorption of the surgical appliance, without the need for further surgical procedure.

8. The procedure of claim 7 further including drilling and tapping a second hole and inserting a second surgical appliance after insertion of the first surgical appliance and draping the soft tissue on both surgical appliances.

9. The procedure of claim 7 wherein the soft tissue and skin being moved is a portion of a brow.

* * * * *